United States Patent
Derand et al.

(10) Patent No.: US 7,238,255 B2
(45) Date of Patent: Jul. 3, 2007

(54) MICROFLUIDIC DEVICE AND ITS MANUFACTURE

(75) Inventors: Helene Derand, Taby (SE); Lars Lundbladh, Taby (SE); Olle Larsson, Stockholm (DE); Lars Rosengren, Vange (SE)

(73) Assignee: Gyros Patent AB, Uppsala (SE)

( * ) Notice: Subject to any disclaimer, the term of this patent is extended or adjusted under 35 U.S.C. 154(b) by 0 days.

(21) Appl. No.: 10/330,602

(22) Filed: Dec. 27, 2002

(65) Prior Publication Data

US 2003/0129360 A1 Jul. 10, 2003

Related U.S. Application Data

(60) Provisional application No. 60/369,174, filed on Apr. 4, 2002.

(30) Foreign Application Priority Data

Dec. 31, 2001 (SE) .................................. 0104460

(51) Int. Cl.
*B32B 37/12* (2006.01)
(52) U.S. Cl. ....................... 156/292; 156/291; 422/100; 422/102
(58) Field of Classification Search ........ 156/290–292; 137/833–834; 204/450–451, 600–601; 428/167
See application file for complete search history.

(56) References Cited

U.S. PATENT DOCUMENTS

| | | | |
|---|---|---|---|
| 4,957,582 A | 9/1990 | Columbus | |
| 5,147,607 A | 9/1992 | Mochida | |
| 5,376,252 A | 12/1994 | Ekstrom et al. | |
| 5,545,280 A * | 8/1996 | Wenz .......................... | 156/234 |
| 5,690,841 A | 11/1997 | Elderstig | |
| 5,773,488 A | 6/1998 | Allmer | |
| 5,932,315 A * | 8/1999 | Lum et al. .................. | 428/172 |
| 5,962,081 A | 10/1999 | Ohman et al. | |
| 5,995,209 A | 11/1999 | Ohman et al. | |
| 6,054,034 A * | 4/2000 | Soane et al. ................ | 204/601 |
| 6,123,798 A | 9/2000 | Gandhi et al. | |
| 6,126,765 A | 10/2000 | Ohman | |
| 6,144,447 A | 11/2000 | Ohman | |
| 6,176,962 B1 | 1/2001 | Soane et al. | |

(Continued)

FOREIGN PATENT DOCUMENTS

WO   IB-94/29400 A1   12/1994

(Continued)

OTHER PUBLICATIONS

International Preliminary Report on PCT/SE 2002/002431.

(Continued)

*Primary Examiner*—Jessica Ward
(74) *Attorney, Agent, or Firm*—Fulbright & Jaworski LLP

(57) ABSTRACT

A method for increasing the yield of functional microchannel structures per microfluidic device in the manufacturing of microfluidic devices each of which comprises a plurality of enclosed microchannel structures, said manufacturing comprising the manufacture of a microfluidic device which comprises enclosed microchannel structures by joining a substrate surface I of a first generally planar plastic substrate I to a substrate surface II of a second generally planar substrate II via a bonding material.

15 Claims, 5 Drawing Sheets

U.S. PATENT DOCUMENTS

| | | | |
|---|---|---|---|
| 6,192,768 B1 | 2/2001 | Wallman et al. | |
| 6,203,291 B1 | 3/2001 | Stemme et al. | |
| 6,284,113 B1 * | 9/2001 | Bjornson et al. | 204/453 |
| 6,322,682 B1 | 11/2001 | Arvidsson et al. | |
| 6,454,970 B1 | 9/2002 | Ohman et al. | |
| 6,524,488 B1 * | 2/2003 | Insley et al. | 210/767 |
| 6,531,206 B2 * | 3/2003 | Johnston et al. | 428/172 |
| 6,620,478 B1 | 9/2003 | Ohman | |
| 6,632,656 B1 | 10/2003 | Thomas | |
| 6,653,625 B2 | 11/2003 | Andersson et al. | |
| 6,717,136 B2 | 4/2004 | Andersson et al. | |
| 6,728,644 B2 | 4/2004 | Bielik et al. | |
| 6,811,736 B1 | 11/2004 | Ohman et al. | |
| 6,812,456 B2 | 11/2004 | Andersson et al. | |
| 6,812,457 B2 | 11/2004 | Andersson et al. | |
| 2002/0092767 A1 * | 7/2002 | Bjornson et al. | 204/451 |
| 2002/0112959 A1 * | 8/2002 | Xue et al. | 204/453 |
| 2003/0044322 A1 | 3/2003 | Andersson | |
| 2003/0047823 A1 | 3/2003 | Ohman | |
| 2003/0053934 A1 | 3/2003 | Andersson | |
| 2003/0054563 A1 | 3/2003 | Ljungstrom | |
| 2003/0082075 A1 | 5/2003 | Agren | |
| 2003/0094502 A1 | 5/2003 | Andersson | |
| 2003/0129360 A1 | 7/2003 | Derand et al. | |
| 2003/0156763 A1 | 8/2003 | Soderman | |
| 2003/0211012 A1 | 11/2003 | Bergstrom | |
| 2003/0213551 A1 | 11/2003 | Derand | |
| 2003/0231312 A1 | 12/2003 | Sjoberg | |
| 2004/0058408 A1 | 3/2004 | Thomas | |
| 2004/0096867 A1 | 5/2004 | Andersson | |
| 2004/0099310 A1 | 5/2004 | Andersson | |
| 2004/0120856 A1 | 6/2004 | Andersson | |
| 2004/0202579 A1 | 10/2004 | Larsson et al. | |

FOREIGN PATENT DOCUMENTS

| | | |
|---|---|---|
| WO | IB-98/32535 A1 | 7/1998 |
| WO | IB-98/45693 A1 | 10/1998 |
| WO | IB-99/56954 A1 | 11/1999 |
| WO | IB-00/50871 A1 | 8/2000 |
| WO | IB-01/30490 A1 | 5/2001 |
| WO | IB-01/54810 A1 | 8/2001 |
| WO | IB-01/97974 A1 | 12/2001 |
| WO | WO 01/97974 * | 12/2001 |

OTHER PUBLICATIONS

U.S. Appl. No. 10/111,822, filed Aug. 16, 2002, Tooke et al.
U.S. Appl. No. 10/849,321, filed May 19, 2004, Fielden et al.
U.S. Appl. No. 10/244,667, filed Sep. 19, 2002, Agren.
U.S. Appl. No. 10/069,827, filed Feb. 26, 2002, Derand et al.
U.S. Appl. No. 09/674,457, filed Jan. 5, 2001, Larsson et al.
U.S. Appl. No. 09/869,554, filed Jun. 28, 2001, Orlefors et al.
U.S. Appl. No. 09/830,475, filed Sep. 24, 2001, Stjemstrom.
U.S. Appl. No. 10/168,942, filed Sep. 25, 2002, Tooke et al.
U.S. Appl. No. 10/957,452, filed Oct. 1, 2004, Ekstrand et al.
U.S. Appl. No. 10/070,912, filed Mar. 13, 2002, Ohman et al.
U.S. Appl. No. 10/402,137, filed Mar. 31, 2003, Kylberg et al.
U.S. Appl. No. 10/030,297, filed Dec. 21, 2001, Derand et al.
U.S. Appl. No. 10/924,151, filed Aug. 23, 2004, Tooke et al.
U.S. Appl. No. 10/513,084, filed Jul. 29, 2005, Holmquest et al.
U.S. Appl. No. 10/999,532, filed Nov. 30, 2004, Ostlin et al.
U.S. Appl. No. 10/867,893, filed Jun. 15, 2004, Derand et al.
U.S. Appl. No. 11/017,252, filed Dec. 20, 2004, Derand et al.
U.S. Appl. No. 10/182,792, filed Jul. 30, 2002, Derand et al.
U.S. Appl. No. 10/450,177, filed Jun. 11, 2003, Ohman et al.
U.S. Appl. No. 10/129,032, filed Apr. 29, 2002, Tormod.
U.S. Appl. No. 09/958,577, filed Nov. 29, 2001, Ulfendahl.
U.S. Appl. No. 10/402,138, filed Mar. 31, 2003, Kylberg et al.
U.S. Appl. No. 10/276,282, filed Aug. 31, 2003, Larsson et al.
U.S. Appl. No. 10/169,056, filed Sep. 25, 2002, Andersson et al.
U.S. Appl. No. 09/937,533, filed Nov. 27, 2001, Larsson et al.
U.S. Appl. No. 11/010,956, filed Dec. 13, 2004, Andersson et al.
U.S. Appl. No. 11/010,977, filed Dec. 13, 2004, Andersson et al.
U.S. Appl. No. 11/010,869, filed Dec. 13, 2004, Andersson et al.
U.S. Appl. No. 11/010,870, Dec. 13, 2001, Andersson et al.

* cited by examiner

MICROFLUIDIC DEVICE AND ITS MANUFACTURE

This application claims priority to SE-0104460-1, which was filed on Dec. 31, 2001, and to U.S. Provisional Application No. 60/369,174, which was filed Apr. 4, 2002.

TECHNICAL FIELD

The present invention concerns a method for the manufacture of a microfluidic device, which comprises a plurality of enclosed microchannel structures. The method comprises joining a substrate surface I of a first generally planar substrate I to a substrate surface II of a second generally planar substrate II via a bonding material. At least one of the substrates exposes a plastic material in the surface to be joined with the other substrate, which preferably also exposes a plastic material in the surface that is used for the joining. Each of surface I and surface II comprises structural parts that together define enclosed microchannel structures when the two substrate surfaces are mated to each other. The invention also concerns in a second aspect a microfluidic device, which can be manufactured by the innovative method as well as by other methods. In this aspect each of one or more of the microchannel structures of the device may be loaded with a liquid aliquot, preferably aqueous, that will be transported within the device.

BACKGROUND OF THE INVENTION

The manufacturing of microfluidic devices by bonding the surfaces of two generally planar substrates together has been described in a number of publications.

U.S. Pat. No. 5,376,252 (Ekström et al.,) vaguely suggests in general terms that certain combinations of material might require gluing for joining the substrates together. In certain variants, walls projecting from the surface of the plastic substrate defined the open microchannel structure. The problems with clogging and the formation of irregularly occurring constrictions were never recognized.

U.S. Pat. No. 4,957,582 (Columbus) suggests to produce a microfluidic device comprising hydrophilic microchannels by using hydrophilic glues.

WO 9424900 (Öhman) suggests to use a gluing solution comprising (a) a solvent not dissolving the substrate surfaces, and (b) a gluing component capable of fusing with the substrate surfaces.

WO 9845693 and U.S. Pat. No. 6,176,962 (Soane et al.,) suggest to use adhesives in combination with particular protocols.

WO 9956954 (Quine) suggests bonding together two generally planar plastic substrates that has been apposed. Bonding is accomplished by heating one of the apposing substrate surfaces above its transition temperature without reaching the transition temperature of the other apposing substrate surface. The "non"-heated surface comprises microscale grooves that defines the stretches of the final microchannel structures. A heat-sensitive meltable texture of bonding material elevating from one of the surfaces could be present outside the grooves.

WO 0050871 (Dapprich) presents microfluidic devices that may be manufactured by adhering the surfaces of two essentially planar substrates to each other. One of the substrates has a microstructured surface that defines the microchannel structures of the final device.

WO 0154810 (Derand et al.,) suggests to thermolaminate a plastic cover to open microchannel structures that are manufactured in a plastic substrate and contain areas of different surface characteristics.

One important and common goal of WO 9424900, WO 9845693 (and U.S. Pat. No. 6,176,962), WO 9956954, WO 0154810, and U.S. Pat. No. 4,957,582 is to minimize irregular deformation of the microchannels caused by intrusion of bonding material or by heat deformation of the channel structures. None of publications account for utilizing channel walls (including rims) that project from the surface of a substrate to minimize the risk for intrusion of bonding material.

WO 9832535 (Lindberg et al.,) and WO 0197974 (Chazan et al.,) concern the problem of minimizing the negative effect of bond void when bonding two planar substrates together. Bond voids depends on irregularities in the surfaces, contaminating particles, unevenly applied pressure during the actual bonding step etc. Bond voids are primarily a problem when rigid substrate materials, such as glass, silicon, quartz, diamonds and certain plastics that have a pronounced rigidity, are combined with bonding processes not utilizing adhesives. The problem with bond voids is normally not at hand for plastic substrates, which typically are flexible. WO 9832535 (Lindberg et al.,) suggests that bond voids can be avoided if the walls of the microchannels are defined by projections in the surface of the substrate and if there are also separate projections defining spacing posts. WO 0197794 (Chazan et al.,) suggests that the disturbing effect of bond voids is avoided by including venting elements in the substrate surfaces in order to neutralize the disturbing effects bond voids might have on the microfluidic channels.

WO 0130490 (Schaevitz et al.,) describes improved sealings of openings in a microfluidic device comprising a number of microchannel structures. Each opening has a collar to which a lid is sealed. The lids are conformable and/or adhesive.

The kind of microfluidic devices defined above has previously been suggested for use as microlaboratories in which a plurality of similar analytical and/or preparative protocols that are in miniaturized form are carried out in parallel (one run per microchannel structure). When going down in channel sizes and liquid volumes, the demands on channel uniformity between different microchannel structures becomes extremely stringent in order to obtain reliable, reproducible and accurate results from the protocols.

The inventors have recognized that the conventional methods of the type described in the first paragraph under the heading "Technical Field" easily cause bonding material, in particular adhesives, to spread into the microchannels in an uncontrolled manner when the substrates are pressed together during the actual bonding process. The risk for creation of irregularly occurring constrictions and/or complete clogging of a microchannel structure is significant and increases with amount of bonding material, in particular liquid adhesives, and contact area between the two substrates. Thus, the first object of the invention aims at minimizing this kind of risks.

A second object is to increase the yield of functioning microchannel structures in microfluidic devices that comprise a plurality of microchannel structures, for instance 2, 3, 4, 5 or more microchannel structures. The yield in this context typically means that $\geq 70\%$, such as $\geq 85\%$ or $\geq 95\%$ or 100% of the microchannel structures in the final microfluidic device are functional, i.e., that they permit through flow of a liquid by having no substantial constriction and/or clogging caused by uncontrolled spreading of bonding material during the manufacturing step comprising bonding of the surfaces to each other. This object in particular applies in case the microchannel structures comprise parts in which the widths and/or depths are in the lower part of the largest of the ranges given above.

By applying an adhesive to one of the surfaces that are to be joined together there will be certain drawbacks. The adhesive will appear also on parts of the inner surfaces of the microchannel structures. This is mostly not desirable and may require post-modification of the inner surfaces. A simple method for avoiding this kind of drawback is desirable. A third object of the invention aims at minimizing this drawback.

BRIEF SUMMARY OF THE INVENTION

The present invention is directed to a method for increasing the yield of functional microchannel structures per microfluidic device in the manufacturing of microfluidic devices each of which comprises a plurality of enclosed microchannel structures, said manufacturing comprising joining a substrate surface I of a first generally planar substrate I to a substrate surface II of a second generally planar substrate II via a bonding material, at least one of the substrate surfaces exposing a plastic material. Specifically, 70% of the enclosed microchannel structures are functional.

In particular, the method comprises the steps of: (i) providing substrate I in a form in which substrate surface I comprises a first relief pattern which defines at least a part of the walls of the enclosed microchannel structures, and substrate II in a form in which substrate surface II has (1) a size that enables coverage of said first relief pattern, and (2) optionally comprises a complementing relief pattern; (ii) apposing substrates surface I and substrate surface II so that enclosed microchannel structures are formed; and (iii) bonding the substrate surfaces together via said relief patterns and said bonding material. The bonding material is an adhesive and is present selectively on the tops of the first relief pattern and/or on the tops of the second relief pattern, if present, and/or on the tops of complementing relief patterns, if present.

In specific embodiments, one of the substrate surfaces comprises a second relief pattern defining at least a part of spacer elements that in the final microfluidic device are positioned between said enclosed microchannel structures, and the other substrate surface optionally contains a complementing relief pattern. Specifically, the first relief patterns are of the same material as the corresponding substrate surface, preferably as an integral part of substrate surface I.

In further embodiments, the first and second relief patterns are on substrate surface I and have tops defining a common top plane. Yet further, the first relief pattern defines the complete walls of the enclosed microchannel structures and the second relief pattern, if present, defines the complete spacer elements the final microfluidic device.

In further embodiments, the depth of a microchannel structure varies within the structure. More particularly, the microchannel structures comprise parts in which the width and/or depth is ≦200 μm. For example, the widths (at the half height) of at least a portion of said walls are in the interval 1-1000 μm. The ratio between the width (at the half height) and the height of the wall (measured from the base surface) is ≧0.1. The height of one or more of said spacer elements or said relief pattern is the same as the depth of at least a portion of an open microchannel structure.

Another embodiment is a microfluidic device comprising a plurality of enclosed microchannel structures that are (a) embedded between substrate surface I of a first generally planar substrate I and substrate surface II of a second generally planar substrate II, at least one of said substrate surfaces exposing a plastic material, and (b) delineated by walls stretching between said substrates, said walls being joined to at least one of said two surfaces via a bonding material and being an integral part of a surface to which it is not joined via a bonding material. The bonding material is selectively present where said walls and spacer elements join a substrate surface without being an integral part thereof.

In specific embodiments, the separate spacer elements (a) are placed between said micochannel structures, (b) are joined to at least one of said two substrate surfaces via a bonding material and are an integral part of a substrate surface to which they are not joined via a bonding material.

Still further, the depth of a microchannel structure varies within the structure. More particularly, the microchannel structures comprise parts in which the width and/or depth is ≦200 μm. The widths (at the half height) of at least a portion of said walls are in the interval 1-1000 μm. The ratio between the width (at the half height) and the height of the walls is ≧1. The height of one or more of said spacer elements or said walls is the same as the depth of at least a portion of a microchannel structure.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1a is a top view, FIG. 1b a cross-sectional view along A-A (exaggerated)

DETAILED DESCRIPTION OF THE INVENTION

Figure 1B:
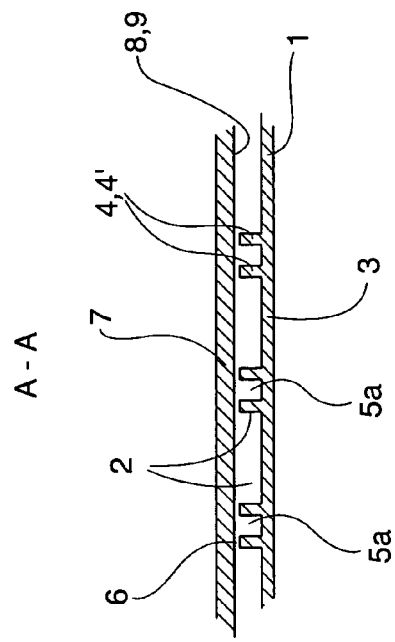
FIGS. 1a, b and c illustrate a microchannels structure of the innovative microfluidic device with a transparent substrate and without spacer elements.
FIG. 1c illustrates typical dimensions in μm.

It is readily apparent to one skilled in the art that various embodiments and modifications can be made to the invention disclosed in this Application without departing from the scope and spirit of the invention.

I. Definitions

As used herein, the use of the word "a" or "an" when used in conjunction with the term "comprising" in the sentences and/or the specification may mean "one," but it is also consistent with the meaning of "one or more," "at least one," and "one or more than one."

In the context of the invention, the term "microfluidic device" means a) a device that comprises a plurality of enclosed microchannel structures, each of which comprises one or more enclosed microchannels and/or microcavities, and b) that these microchannel structures are used for transporting and processing liquid aliquots that are in the microliter range and may contain reactants including e.g., analytes and reagents. The liquid aliquots are typically aqueous. The transporting and processing are typically part of an analytically and/or a preparative process protocol. The number of microchannel structures in a device may be $\geq 5$, such as $\geq 10$ or $\geq 50$ and are typically $\leq 1000$, such as $\leq 500$. This kind of devices typically is disc-like, preferably with an axis of symmetry (Cn where n is an integer 2, 3, 4, 5, 6 . . . ∞) perpendicular to the plane of the disc. Disc-like microfluidic devices having this symmetry feature may have rectangular shape, such as squaric shape, and other polygonal shapes for which this symmetry apply. A certain variant is the circular format (n=∞). In particular disc-like devices of the types mentioned may be spun around the axis of symmetry in order to transport liquids within the microchannel structures by the use of centrifugal force. The spin axis does not need to coincide with the axis of symmetry and may or may not intersect the disc plane. The liquid aliquots are typically aqueous and thus include water and mixtures of water with water-miscible organic solvents.

In the context of the invention, the term "microchannel structure" typically comprises microchannels with depths and/or widths that are $\leq 1,000$ μm, such as $\leq 500$ μm $\leq 200$ μm or $\leq 100$ μm or $\leq 50$ μm. In addition to microchannels for transport of liquids there may also be separate channels that vent to ambient atmosphere, either for inlet or outlet of air. The widths and/or depths of venting channels may be in the same range as the other channels, but many times it may be advantageous to make them more narrow and/or more shallow than the channels used for liquid transportation (e.g., with width and/or depths $\leq 500$ μm $\leq 200$ μm or $\leq 100$ μm or $\leq 50$ μm).

The term "microliter range" means liquid aliquots $\leq 1000$ μl, i.e., the range includes the nanoliter range ($\leq 1000$ nl) as well as the picoliter range ($\leq 1000$ pl).

The term "selectively" in this context means that bonding material is applied to the top surfaces of at least the first relief pattern in substrate surface I and/or its complementary relief pattern in substrate surface II with essentially no bonding material distributed to parts of the surfaces that are to define inner surfaces of the microchannel structures to be formed. The term includes that parts of a substrate surface that are not part of the microchannel structures may be contaminated with bonding material.

The term "height" in the context of the invention refers to the height measured relative to the base surface outside a microchannel and in close proximity to the position for which the height is measured.

The term "width" refers to the width at the half height of a wall, if not otherwise indicated.

The term "wall" in the context of the first relief pattern means side walls of the microchannels defined by this relief pattern, if not otherwise is apparent from the context. Top and bottom walls of the microchannel structures extend essentially in the same general direction as substrate surface I and II.

II. Microfluidic Devices

Microfluidic devices may have microchannel structures in one or more planes. The present invention concerns the formation of microchannel structures in a plane that corresponds to the interface between two apposing generally planar substrates. This does not exclude that the final device also may have one, two or more microchannel structures in other planes that may be placed above, below or at a certain angle in relation to the plane defined by the interface created in the present innovative method. These other microchannel structures may also be defined between two generally planar substrates that have been joined together. Microchannel structures that are present in different planes may form a completed microchannel structure in which a complete process protocol can be performed.

Microchannel structures may communicate with each other, both within a plane and between different planes. This communication may be via transport channels for liquids. There may also be venting channels for inlet of ambient atmosphere or for outlet to ambient atmosphere of air displaced by liquids during operation of the device. Venting channels may be common for several microchannels through which liquid aliquots are to be transported.

The inventors have recognized that the objects of the invention can be achieved in case the walls (4) of the microchannel structures (5) are defined by a first relief pattern (4') projecting from a base surface I (3) of substrate surface I (2) and/or from a base surface II (9) of substrate surface II (8). The inventors have also recognized that the microchannel structures (5) may be stabilized if a second relief pattern (10') corresponding to spacer elements (so called distance holders) (10) are present in those parts of substrate surface I and/or substrate surface II that are not becoming part of a final microchannel structure. In other words, the distance holders deriving from the second relief pattern are in the final microfluidic device located between individual microchannel structures. By selectively applying bonding material on the tops (6) of these relief patterns, the inventors have minimized the risk for pressing bonding material, in particular adhesives, into the microchannels during the bonding process. Bond voids are in principle not formed meaning that the venting elements of WO 0197974 (Chazan et al.,) are not needed.

The first aspect of the invention is a method utilizing these findings. A preferred embodiment of the first aspect thus is a method for the manufacture of a microfluidic device, which comprises a plurality of enclosed microchannel structures. The method comprises joining a substrate surface I of a first generally planar substrate I to a substrate surface II of a second generally planar substrate II via a bonding material. At least one of the substrates exposes a plastic material in the surface to be joined with the other substrate, which preferably also exposes a plastic material in the surface that is used for the joining. Each of surface I and surface II comprises structural parts that together define enclosed microchannel structures when the two substrate surfaces are mated to each other.

The method is characterized in comprising the steps of (i) providing (a) substrate I (1) in a form in which substrate surface I (2) comprises a first relief pattern (4') (raised pattern) which defines at least a part of the walls (4) of the microchannel structures (5), and (b) substrate 11 (7) in a form in which substrate surface II (8) (1) has a size that enables coverage of said first relief pattern (4'), and (2) optionally comprises a complementing relief pattern comprising the remaining parts of the walls if the first relief pattern (4') is incomplete, (ii) apposing substrates surface I (2) and substrate surface II (8) so that the enclosed microchannel structures (5) defined by the first relief pattern (4') and, if present, its complementing relief pattern, are formed, and (iii) applying conditions that will bond the surfaces together via said bonding material and via said relief pattern (s) without deforming said microchannel structures. This aspect of the invention also concerns a method for minimizing the risks and/or to increase the yield per device of functioning microchannel structures intended for liquid flow.

In preferred variants, substrate surface I (2) and/or substrate surface II (8) also may comprise a second relief pattern (10') (raised pattern) defining at least a part of the spacer elements (10) (distance holders) which have been discussed above. In the case the spacer elements are not completely defined by this second relief pattern, the remaining parts of them are defined by a complementing relief pattern in the other substrate surface. In a preferred variant in which there are spacer elements, the second relief pattern (10') is part of substrate surface I (2), i.e., the first and second relief patterns (4' and 10') are present in the same substrate surface. It follows that the tops of each relief pattern that is present are used for the bonding.

In the most preferred variants, the first and second relief patterns define the walls (4) of the microchannel structures and the spacer elements (10) (if present), respectively, and are present in substrate surface I (2). There is thus no need in this embodiment for including complementing relief patterns as discussed above. The top planes defined by the tops of the first and second relief pattern are essentially planar and coincide. The walls of the microchannel structures in this embodiment typically correspond to rims delineating those parts of base surface I that constitute the "bottom" surfaces of the microchannel structures.

Figure 1A:
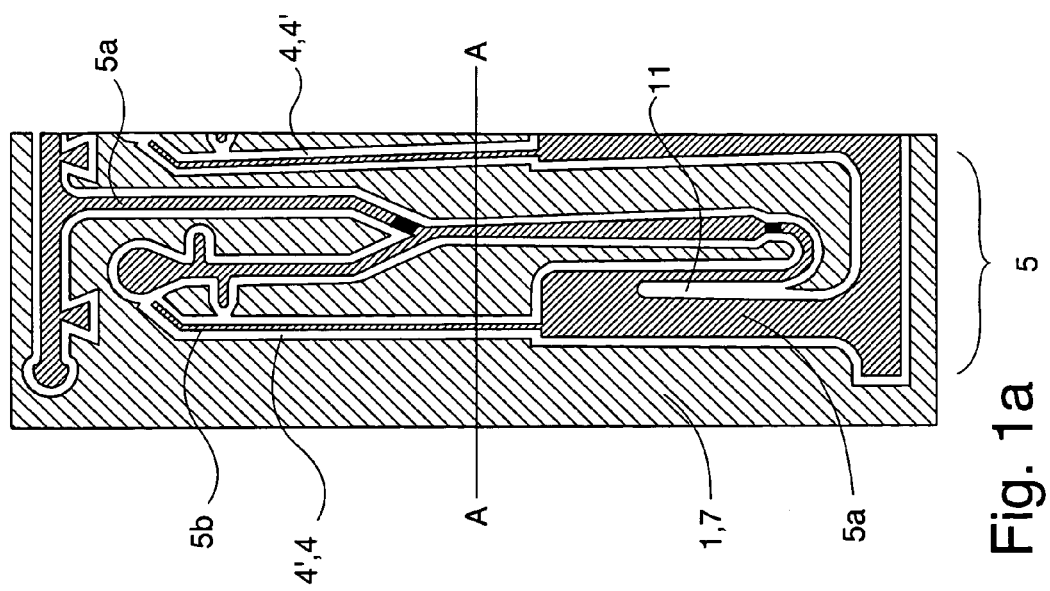
Figure 1C:
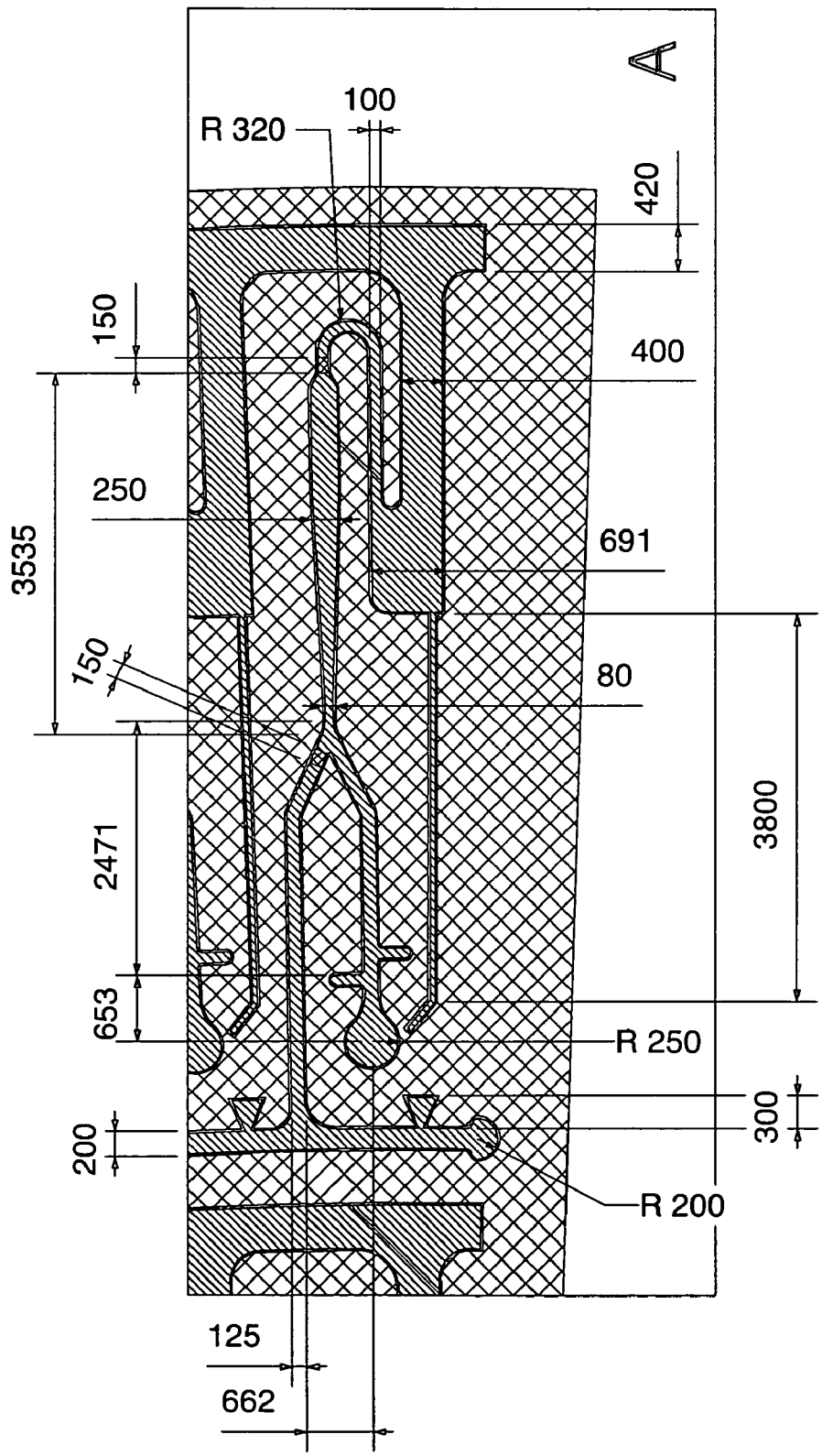
Figure 2:
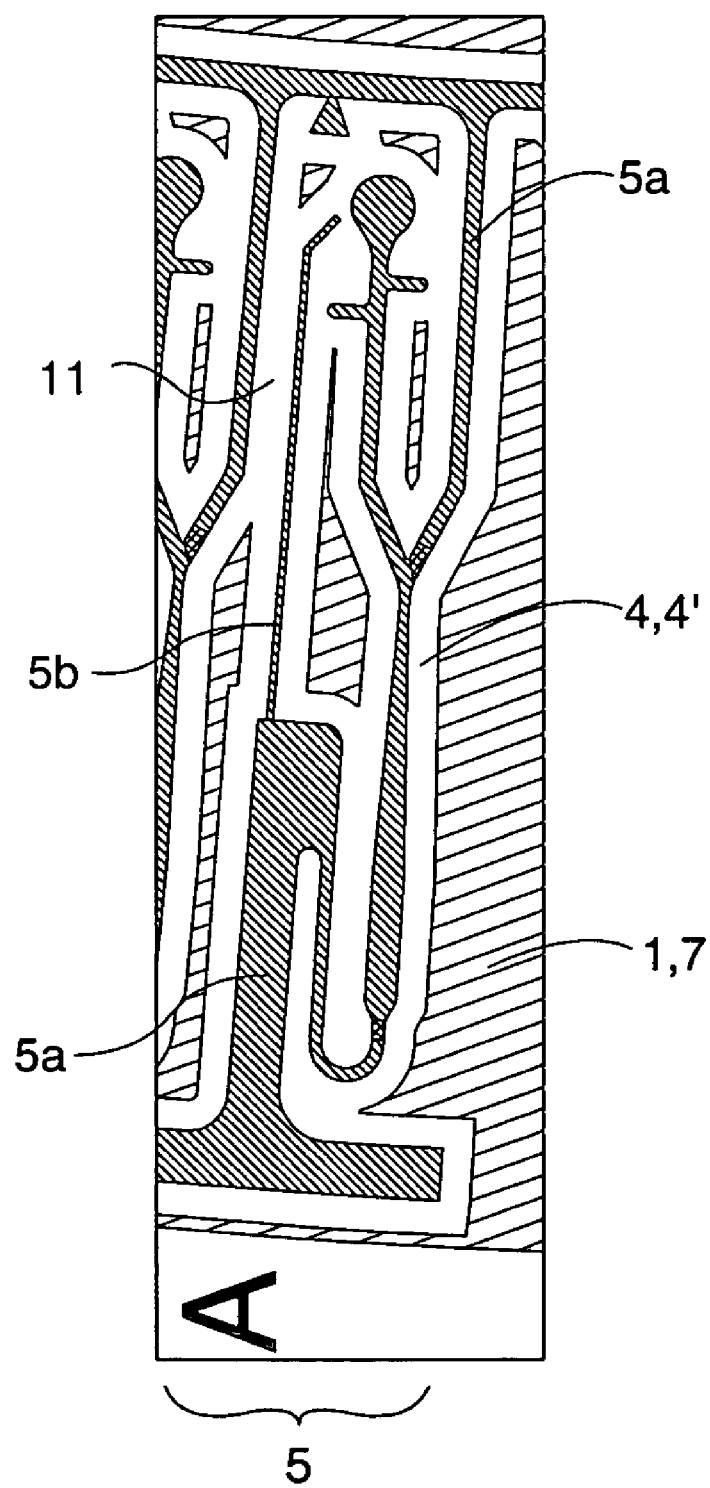
FIG. 2 illustrates a similar microchannel structure as in FIGS. 1a-c with thicker walls.
Figure 3:
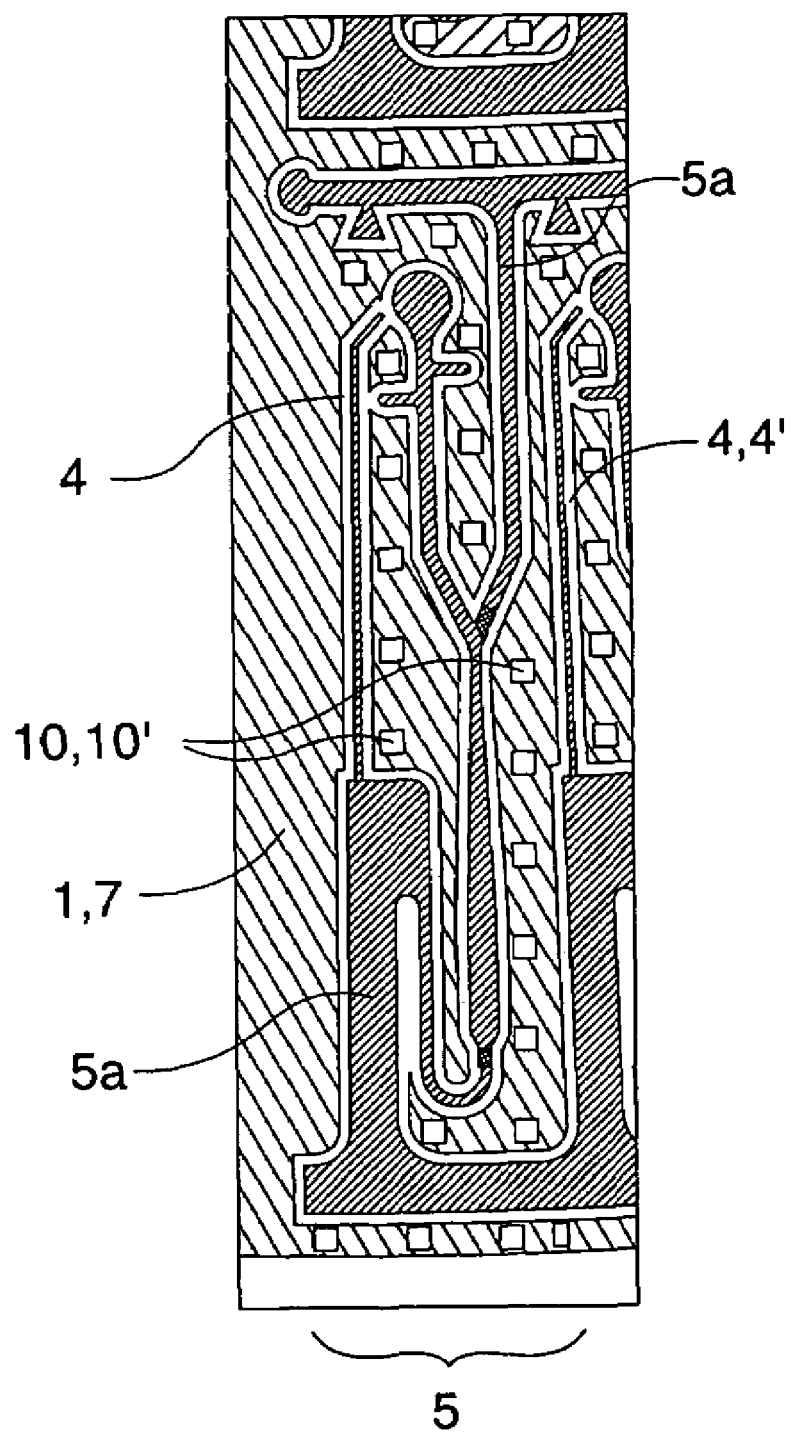
FIG. 3 illustrates a microchannel structure of the innovative microfluidic device with separate spacer elements.

As illustrated in FIGS. 1a and b, FIG. 2 and FIG. 3, the final microfluidic device thus may comprise a first generally planar substrate I (1) comprising a first substrate surface I (2) with a distinct base surface I (3) from which the walls (4) (first relief pattern (4')) of a microchannel structure (5) project. The microchannel structure (5) comprises microchannels for transportation of liquids (5a) or for venting to ambient atmosphere (5b). Apposed to the tops (6) of the walls (4) there is a second generally planar substrate (7) that may be transparent as shown in the figures. The second substrate comprises a second substrate surface (II) (8) with a base surface II (9) which in the variant shown is devoid of relief pattern and coincides with and is indistinguishable from substrate surface II. The walls (4) of the microchannel structure (5) and possibly also separate spacer elements (10) (second relief pattern (10')) extend between the two base surfaces, which for the preferred variants illustrated in the figures extends from base surface I to substrate surface II.

The figures illustrate preferred variants in which the tops (6) of the first relief pattern (4') define a common essentially planar top plane. In the case substrate surface I (2) also comprises a second relief pattern (10') which defines the spacer elements (10), the tops of this second relief pattern preferably coincide with the common top plane defined by the tops of the walls (4) (first relief pattern (4')).

The walls (4) of microchannel structures and the separate spacer elements (10) are formed when a corresponding relief pattern elevating from a base surface of one of the substrates meets the substrate surface of the other substrate. In a general sense, a base surface (3 or 9) is thus a substrate surface (2 or 8) without a relief pattern and a substrate surface (2 or 8) is a base surface (3 or 9) with a superimposed relief pattern (if present).

The dimensions of the walls of the microchannels and the spacer elements and accordingly also the elevated parts of the relief patterns will depend on various factors. Factors to account for are material in the substrates, design of the individual microchannel structures, such as the width and the depth of the microchannel structures, etc. The width of the walls of the microchannel may differ between channels as well as within channels as illustrated in the figures. If different parts of a microchannel are close to each other it is practical to merge the delineating walls into a common wall (11).

Typically, the width of at least a portion of the walls is $\geq 1$ µm, such as $\geq 10$ µm, and/or $\leq 1000$ µm, such as $\leq 500$ µm. For walls that are common for two neighboring microchannels these limits should be doubled. The ratio between the width and the height of the wall is typically $\geq 0.1$, such as $\geq 1$ or $\geq 5$. The microchannels, the walls and the spacer elements, if present, occupy typically $\leq 95\%$, such as $\leq 90\%$ or $\leq 80\%$ or $\leq 50\%$ or $\leq 10\%$, or $\geq 1\%$, such as $\geq 5\%$, of the smallest of substrate surfaces I and II.

The height of one or more spacer elements or of the walls of the microchannel structures is typically the same as the depth of at least a portion of an open microchannel structure. This rule primarily relates to devices and methods utilizing substrate surfaces obtained by replicating against a matrix comprising the inverse relief pattern. The depth of a microchannel structure may vary within a microchannel structure.

The final microfluidic device typically comprises 1, 2, 3, 4, 5 or more separate spacer elements per microchannel structure with an upper limit typically being 300 or more separate spacer elements per microchannel structure. A separate spacer element typically has a cross sectional area that is in the interval of 1 µm2-10 mm$^2$, such as 10 µm2-10 mm$^2$ or 100 µm$^2$-1 mm$^2$, at its smallest part and is physically separated from the walls of the microchannels and from the edges of the substrate surfaces. The cross-sectional area of a spacer element may be squaric, triangular, rounded, elongated etc. The cross-sectional area and number of the spacer elements depend on factors such as the area of the substrate surfaces, number of microchannels structures, geometric arrangement of the spacer elements and/or the microchannel structures total, material of the substrates etc.

The substrates may be made from different materials, such as plastics including but not limiting to elastomers, such as rubbers including silicone rubbers (for instance poly dimethyl siloxane) etc. From the manufacturing point of view, substrate surfaces exposing a relief pattern in plastic material is preferred because the costs for plastics are normally low and mass production can easily be done, for instance by replication. Typical manufacturing processes involving plastic material are photolithography, laser ablation, replication by embossing, molding, casting etc. For replication see for instance U.S. Pat. No. 5,376,252 (Danielsson et al.,), which is incorporated by reference herein. Preferred plastic materials are polymethyl methacrylate (PMMA), polycarbonates and other thermoplastic materials, e.g., plastic material based on monomers which consist of a polymerizable carbon-carbon double or triple bonds and saturated branched straight or cyclic alkyl and/or alkylene groups. Typical examples are Zeonex™ and Zeonor™ from Nippon Zeon, Japan. See for instance WO 0056808 (Larsson et al.,) which is hereby incorporated by reference.

Surfaces that are to define inner surfaces of microchannel structures may be made hydrophilic in advance of step (i) or after step (iii). If in advance, one or both of the substrate surfaces provided in step (i) is/are of a suitable hydrophilicity, at least at those parts that will define inner surfaces of microchannel structures after step (iii). Typical hydrophilization protocols are outlined in WO 0056808, WO 0147637, or U.S. Pat. No. 5,773,488 (Gyros AB) which are incorporated by reference herein. The hydrophilicity (wettability) of inner surfaces are given in these publications, i.e., an aqueous liquid, such as water, having a volume within any of the intervals given herein should be drawn by capillarity into one of the microchannel structures. Where appropriate hydrophobic surface breaks (e.g., as anti-wicking means and/or valves) are preferably introduced before step (i) as outlined in WO 9958245 and WO 0274438. See also WO 0185602 (Åmic A B & Gyros A B). Hydrophobic surface breaks may also be introduced after step (iii).

The exact demand on hydrophilicity (wettability) of inner surfaces of a microchannel structure may vary between different functional units of a structure. Except for local hydrophobic surface breaks (hydrophobic=liquid contact angle>90°), the liquid contact angel for at least two or three inner walls of a micro conduit in a particular functional unit may be wettable (=hydrophilic=liquid contact angle$\leq$90°) for the liquid to be transported, with preference for liquid contact angels that are $\leq$60°, such as $\leq$50° or $\leq$40° or $\leq$30° or $\leq$20°. In the case one or more inner walls have a higher liquid contact angle, for instance is non-wettable (hydrophobic), this can be compensated by a lowered liquid contact angle on the other walls. This may be particularly important if one of surface I and II is hydrophobic. These figures for wettability in most cases apply to one or more inner surfaces (bottom surface, top surface, side wall surfaces) throughout a complete microchannel structure, except for valves and venting channels not intended for liquids. The liquid contact angles given above refer to equilibrium contact angles and measured at the temperature of use, for instance room temperature such as +25° C.±5° C.

In preferred variants, substrate I is made in plastic material, for instance by the techniques referred to above. In the preferred variants substrate II is also made in plastic material.

The bonding material may be part of or separately applied to substrate surface I and/or substrate surface II. As illustrated in FIG. 1b the bonding material is preferably present on the tops of a relief pattern, for instance the tops of the first relief pattern and/or of the second relief pattern, if present, and/or on one or both of the complementing relief patterns. In this variant, the bonding material is placed selectively on tops of relief patterns and not on surface parts that will be within the final microchannels.

The bonding material may be the same plastic material as is present in a substrate surface, provided this plastic material can work as a bonding material. Other useful bonding materials are various kinds of adhesives which fit to the material exposed in the substrate surfaces and to the intended use of the final device. Typically adhesives may be selected amongst melt-adhesives, and curing adhesives etc. Illustrative examples of curing adhesives are thermo-curing, moisture-curing, and bi-, three- and multi-component adhesives.

In principle, the adhesive may be selected as outlined in U.S. Pat. No. 6,176,962 and WO 9845693 (Soane et al.,) which are hereby incorporated by reference. Thus, suitable bonding materials include, but are not limited to elastomeric adhesive materials and curable bonding materials. These kinds of bonding material as well as others may be in liquid form when applied to a substrate surface. Bonding materials including adhesives thus comprises liquid curable adhesive material and liquid elastomeric material. After application, the adhesive material is rendered more viscous or non-flowable for instance by solvent removal or partial curing before the other substrate is contacted with the adhesive. Liquid form includes material of low viscosity and material of high viscosity. Curable adhesive includes, but are not limited to polymerizable adhesives and activatable adhesives.

As indicated above step (i) may comprise as a separate step application of the bonding material to substrate surface I and/or substrate surface II. Step (ii) includes that any complementing relief pattern is matched to the corresponding relief pattern in the apposing surface, so that enclosed microchannel structures or complete spacer elements, respectively, are formed. Step (iii) includes that bonding conditions are applied. The conditions are typically within ranges given by the manufacturer of the adhesive, with appropriate care taken not to deform the relief pattern defining the walls of the microchannel structures. See for instance WO 9424900 (Ove Öhman), WO 9845693 (and U.S. Pat. No. 6,176,962) (Oane et al.,), WO 9956954 (Quine), WO 0154810 (Dérand), and U.S. Pat. No. 4,957,582 (Columbus). Typically this step comprises pressing substrate surface I and substrate surface II together and applying the specific conditions required by a selected bonding material, for instance heat if it is a melt-adhesive, UV irradiation if it is a UV curing adhesive, moisture if it is a moisture-curing adhesive etc. In many cases heating may speed up the curing reaction.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

This example illustrates the manufacture of a microfluidic device made of a polycarbonate disc (substrate I) with microchannel structures to which a lid (substrate II) made from polycarbonate was bonded using a photocurable bonding material. Walls projecting from a base surface of substrate I as illustrated in FIGS. 1a and b, and FIG. 2 defined the microchannel structures. Certain variants with spacer elements (FIG. 3) were also managed. The bonding material was photocurable. The figures show enclosed microchannels structures (5), walls (4) and spacers (10).

A thin layer (1-10 μm) of the bonding material (UVF 00006, Akzo Nobel Inks) was applied onto the structured disc (substrate I) using a flexoprinter for CD/DVD (Pinto, Lyrec, Denmark). The lid (with inlet/outlet holes) (substrate II) was carefully positioned on top to form a closed structure. Curing of the bonding material was achieved using a UV lamp. As seen in FIGS. 1a and b, FIG. 2 and FIG. 3 non-clogged enclosed microfluidic channels were formed. Water is transported through the enclosed microchannel structures.

Example 2

Figure 4A:
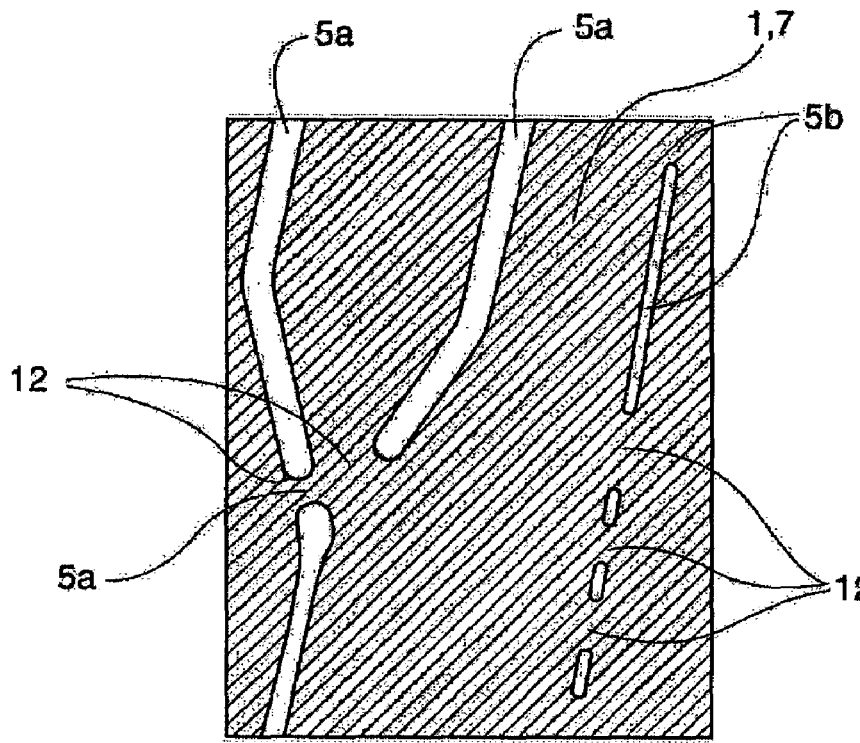
FIGS. 4a and b illustrate a comparison between microchannel structures in a device produced according to the background technology (FIG. 4a) and according to the instant innovative method (FIG. 4b).
Figure 4B:
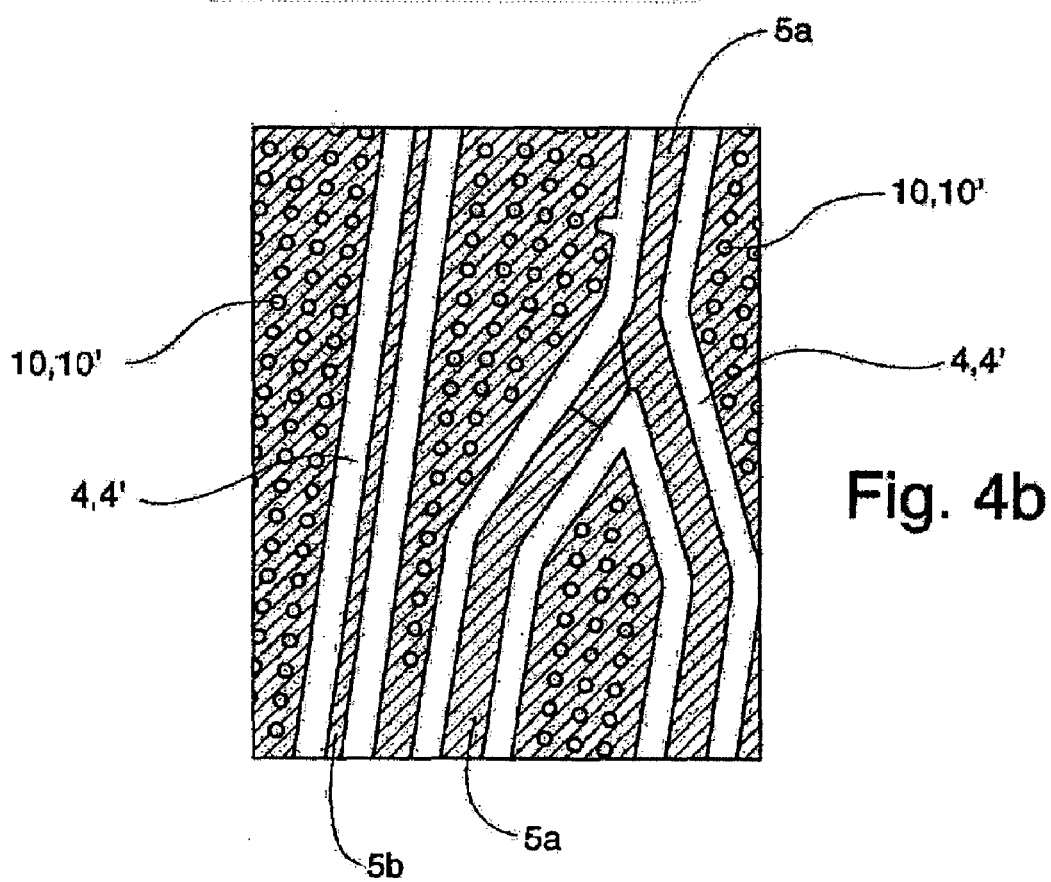

This example illustrates a comparison between the manufacture of a nonfunctioning microfluidic device according to the prior art technique (FIG. 4a) and of a functioning microfluidic device according to the invention (FIG. 4b). Substrate I comprised open microchannel structures and was a polycarbonate disc. Substrate II was a lid made from polycarbonate. The bonding material was photocurable. FIGS. 4a and b show enclosed microchannel structures (5), walls (4, only in FIG. 4b) and spacer elements (11, only in FIG. 4b).

A thin layer (1-10 μm) of the bonding material (UVF 00006, Akzo Nobel Inks) was applied onto the structured disc using a flexoprinter for CD/DVD (Pinto, Lyrec, Denmark). The lid (with inlet/outlet holes) was carefully positioned on top to form a closed structure. Curing of the bonding material was achieved using a UV lamp. Although the same procedure as in example 1 was used for applying adhesive onto this substrate, adhesive was found to flow into the channels and plug them completely, as seen in FIG. 4a (12). The inventors were not able to transport any water through these channels. As illustrated in FIG. 4b, the inventive method resulted in a lower risk for clogged microchannels.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for increasing the yield of functional microchannel structures per microfluidic device in the manufacturing of microfluidic devices each of which comprises a plurality of enclosed microchannel structures having walls, said structures are used to transport and process aliquots of liquids that are in the μl-range and contain reagents and/or analytes, said manufacturing comprising joining a substrate surface I of a first generally planar substrate I to a substrate surface II of a second generally planar substrate II via a bonding material, at least one of the substrate surfaces exposing a plastic material, wherein said method comprises the steps of:

(i) providing substrate I in a form in which substrate surface I comprises a first raised relief pattern which defines at least a part of the walls of the enclosed microchannel structures, and substrate II in a form in which substrate surface II has a size that enables coverage of said first relief pattern, and optionally comprises a raised complementing relief pattern to the first relief pattern which complementing relief pattern defines the remaining part of said walls, wherein one of the substrate surfaces comprises a second raised relief pattern defining at least a part of spacer elements that in the final microfluidic device a) are positioned between said enclosed microchannel structures, and b) are physically separated from the walls of the microchannel structures by a cavity defined by the substrate surfaces, the spacer elements and the walls, wherein the cavity separating the spacer elements from the walls is contiguous around the entire spacer element perimeter, and the other substrate surface optionally contains a raised complementing relief pattern to the second relief pattern which complementing relief pattern defines the remaining part of said spacer elements, and said first and second relief patterns are of the same material;

(ii) apposing substrate surface I and substrate surface II so that a) the enclosed microchannel structures are formed between surface I and surface II by the first raised relief pattern together, if present, with its optional complementing raised relief pattern, and b) said spacer elements are formed between substrate surface I and substrate surface II by the second raised relief pattern and, if present, its optional complementing raised relief pattern, and (iii) bonding the substrate surfaces together via said bonding material, wherein ≧70% of the enclosed microchannel structures are functional.

2. The method of claim 1, wherein said bonding material is present selectively on the tops of the first relief pattern, on the tops the second relief pattern, or on the tops of complementing relief patterns.

3. The method of claim 1, wherein the microchannel structures comprise parts in which the width and/or depth is ≦200 μm.

4. The method of claim 1, wherein the first and second relief patterns are on substrate surface I and have tops defining a common top plane.

5. The method of claim 1, wherein the first and second relief patterns are an integral part of substrate surface I.

6. The method of claim 1, wherein the bonding material is an adhesive.

7. The method of claim 1, wherein the widths of at least a portion of said walls are in the interval of 1-1000 μm.

8. The method of claim 1, wherein the ratio between the width and the height of the wall is ≧0.1.

9. The method of claim 1, wherein the depth of a microchannel structure varies within the structure.

10. The method of claim 1, wherein said spacer elements are physically separated from the edges of the substrate surface on which the second raised relief pattern is present.

11. The method of claim 1, wherein said microchannels, walls and spacer elements occupy ≦90% of the smallest of substrate surfaces I and II.

12. The method of claim 1, wherein the microchannels walls and the spacer elements are physically separated by an area of substrate surface lacking a raised relief pattern.

13. The method of claim 1, wherein the first relief pattern defines the complete walls of the enclosed microchannel structures in the final microfluidic device.

14. The method of claim 13, wherein the second relief pattern defines the complete spacer elements.

15. The method of claim 14, wherein the height of one or more of said spacer elements and/or said walls are/is the same as the depth of at least a portion of an open microchannel structure.

* * * * *